(12) United States Patent
Schramm et al.

(10) Patent No.: US 8,119,620 B2
(45) Date of Patent: Feb. 21, 2012

(54) DOSAGE FORM FOR HORMONAL CONTRACEPTION

(75) Inventors: Georg Schramm, Stolberg (DE); Eric-Paul Paques, Aachen (DE)

(73) Assignee: Gruenenthal GmbH, Aachen (DE)

(*) Notice: Subject to any disclaimer, the term of this patent is extended or adjusted under 35 U.S.C. 154(b) by 206 days.

(21) Appl. No.: 12/118,137

(22) Filed: May 9, 2008

(65) Prior Publication Data

US 2008/0261934 A1    Oct. 23, 2008

Related U.S. Application Data

(63) Continuation of application No. PCT/EP2006/010631, filed on Nov. 7, 2006.

(30) Foreign Application Priority Data

Nov. 9, 2005 (DE) .......... 10 2005 053 771

(51) Int. Cl.
*A01N 45/00* (2006.01)
*A61K 31/56* (2006.01)

(52) U.S. Cl. ...................... 514/171; 514/177

(58) Field of Classification Search .......... 514/171, 514/177
See application file for complete search history.

(56) References Cited

U.S. PATENT DOCUMENTS 5,461,041 A * 10/1995 Bergink et al. ............ 514/179
2005/0267083 A1 12/2005 Schramm et al.
2006/0089338 A1 4/2006 Schramm et al.

FOREIGN PATENT DOCUMENTS

| DE | 10 2004 026 671 A1 | 12/2005 |
| WO | WO 99/53910 | * 10/1999 |
| WO | WO 99/53910 A2 | 10/1999 |
| WO | WO 00/44385 A1 | 8/2000 |
| WO | WO 2005/115349 A1 | 12/2005 |

OTHER PUBLICATIONS

"Fortifying Oral Contraceptives with Folic Acid", AWHONN Lifelines, Association of Women's Health, Obstetric and Neonatal Nurses, XX, US, vol. 8, Issue 1, Feb. 2004, pp. 12-13, XP009052123.
German Search Report dated Sep. 21, 2006 with English translation of relevant portion (Ten (10) Pages).
International Search Report dated Mar. 20, 2007 with English translation of relevant portion (Eleven (11) Pages).
Form PCT/IB/338 & Form PCT/IPEA/409 (International Preliminary Report on Patentability) (seven (7) pages).

* cited by examiner

*Primary Examiner* — Marcos Sznaidman
(74) *Attorney, Agent, or Firm* — Crowell & Moring LLP

(57) ABSTRACT

A dosage form for hormonal contraception containing a specific number of gestagen-containing daily units A and a specific number of gestagen-containing daily units B for uninterrupted, daily, oral administration of daily units A and then immediately subsequently of daily units B, wherein the daily units A in each case contain at most 200 μg of folic acid and the daily units B contain >200 μg up to the maximum permissible amount of folic acid for women.

15 Claims, No Drawings

DOSAGE FORM FOR HORMONAL CONTRACEPTION

CROSS REFERENCE TO RELATED APPLICATIONS

This application is a continuation of international application no. PCT/EP2006/010631, filed Nov. 7, 2006 designating the United States of America and published in German on May 18, 2007 as WO 2007/054258, the entire disclosure of which is incorporated herein by reference. Priority is claimed based on Federal Republic of Germany patent application no. DE 10 2005 053 771.5, filed Nov. 9, 2005.

BACKGROUND OF THE INVENTION

The present invention relates to a dosage form for hormonal contraception consisting of a specific number of hormone-containing daily units A and of 7-3 hormone-containing daily units B, the hormone component of which in each case consists solely of a gestagen, for uninterrupted daily, oral administration of the hormone-containing daily units A, immediately followed by uninterrupted daily, oral administration of the hormone-containing daily units B to women, characterised in that the hormone-containing daily units A in each case contain folic acid in a daily amount of up to at most 200 µg and the hormone-containing daily units B in each case contain folic acid in a daily amount of more than 200 µg up to the maximum permissible amount of folic acid for women.

Hormonal contraceptives based on a gestagen as the hormone component are known as the gestagen pill.

It is suspected that taking these gestagen-based hormonal contraceptives over an extended period may lead to a deficiency of folic acid. This deficiency may lead to cardiovascular diseases, for example.

It is also known that if pregnancy occurs within a short time after stopping taking such hormonal contraceptives, there is a risk that the deficiency of folic acid may lead to neural tube defects in the embryo. Since the neural tube develops in the first weeks of pregnancy, it is particularly advantageous to ensure that folic acid is taken prior to conception.

If, therefore, a woman stops taking the gestagen pill because she wants to have a child and she falls pregnant in the first cycle after stopping the gestagen pill, it is particularly important to ensure an appropriately large amount of folic acid in the period directly after stopping taking the gestagen pill.

There is therefore a need to provide hormonal contraceptives based on a gestagen as the only hormone component with folic acid in such a manner that the added amount of folic acid is adapted to the variable requirements over the time during a pill-taking cycle and thereafter.

The combination of hormonal contraceptives and folic acid is already known from WO 99/53910. The amount of folic acid per hormonal daily dose is only adapted in accordance with the variable requirement for folic acid according to a woman's advancing age. No account is, however, taken of the variable requirement for folic acid over the pill-taking cycle of a contraceptive.

SUMMARY OF THE INVENTION

It was therefore an object of the present invention to provide a dosage form for hormonal contraception based on only one gestagen as the hormone component, which dosage form takes account of the variable requirement for folic acid during the hormonal pill-taking cycle.

This object has been achieved by providing the dosage form for hormonal contraception according to the invention consisting of a specific number of hormone-containing daily units A and of 7-3 hormone-containing daily units B, the hormone component of which in each case consists solely of a gestagen, for uninterrupted daily, oral administration of the hormone-containing daily units A, immediately followed by uninterrupted daily, oral administration of the hormone-containing daily units B to women, characterised in that the hormone-containing daily units A in each case contain folic acid in a daily amount of up to at most 200 µg and the hormone-containing daily units B in each case contain folic acid in a daily amount of greater than 200 µg up to the maximum permissible amount of folic acid for women.

Women of child-bearing age have a daily folic acid requirement which may be adequately met by a healthy diet. Taking hormonal contraceptives containing gestagens over an extended period may lead to an additional folic acid requirement, which may likewise be met by a healthy diet. However, it is advisable to provide women with a daily dose of the minimum effective daily amount of folic acid.

Accordingly, the hormone-containing daily units A of the dosage form according to the invention may each comprise a daily amount of folic acid corresponding to this minimum effective daily amount of folic acid. Preferably, the hormone-containing daily units A of the dosage form according to the invention contain 0 to 200 µg of folic acid, particularly preferably 5 to 200 µg of folic acid.

The hormone-containing daily units A of the dosage form according to the invention may also not comprise an addition of folic acid, but an addition of folic acid is preferred.

To ensure that a woman consumes the necessary amount of folic acid or that her increased folic acid requirement at least at the beginning of pregnancy is met as quickly as possible if she decides to try for a baby, so avoiding possible damage to the embryo due to a folic acid deficiency, the hormone-containing daily units B of the dosage form according to the invention contain folic acid in an amount of more than 200 µg up to the maximum permissible daily amount of folic acid for women, preferably up to 5 mg of folic acid per daily unit, particularly preferably of more than 200 µg to 5 mg of folic acid, very particularly preferably up to the maximum permissible daily amount of folic acid for fertile women.

Thanks to the addition of folic acid to the final 7-3 hormone-containing daily units of a pill-taking cycle, namely the hormone-containing daily units B of the dosage form according to the invention, in amounts up to the maximum permissible amount for fertile women, it is possible while these hormone-containing daily units B are still being taken to increase the concentration of folic acid in a woman's body to such an extent that, should taking of the gestagen contraceptive be stopped and a subsequent pregnancy occur, the increased requirement for folic acid in a woman's body at the onset of pregnancy is ensured as early as possible.

The hormone-containing daily units A of the dosage form according to the invention preferably each contain the same amount of folic acid. This also applies to the hormone-containing daily units B, which likewise each contain the same amount of folic acid, this amount however being greater than the amount contained in the hormone-containing daily units A.

The folic acid may also be present in the dosage form according to the invention as a pharmaceutically safe salt, preferably as a sodium, potassium or magnesium salt, or as a corresponding derivative. Suitable derivatives of folic acid include mono- or diesters, wherein the diesters may be differently or identically esterified. An alcohol residue which is preferably suitable is a short-chain $C_1$-$C_8$ alkyl group, such as methyl, ethyl, propyl or butyl, a branched, short-chain $C_3$-$C_8$ alkyl group, such as isopropyl, isobutyl or sec.-butyl, a cycloalkyl group, such as cyclopentyl or cyclohexyl, an aryl group, such as phenyl or substituted phenyl having 1-2 substituents, for example having a lower alkyl or haloalkoxyl group, or an aralkyl group having a $C_1$-$C_8$ alkyl group and an aryl group, such as phenyl or substituted phenyl.

In addition, the hormone-containing daily units B and optionally the hormone-containing daily units A may contain further vitamins or minerals in addition to the folic acid. Preferably, no further additions of this kind are made.

The number of gestagen-containing daily units of a dosage form according to the invention may correspond to a woman's natural monthly menstrual cycle. In this case, the dosage form according to the invention contains 21 to 25 hormone-containing daily units A to be taken orally daily without interruption and 7 to 3 hormone-containing daily units B to be taken daily without interruption immediately subsequently.

However, it is also possible for the total number of hormone-containing daily units A to correspond to more than a woman's natural monthly cycle, such that a dosage form according to the invention may contain hormone-containing daily units A to be taken without interruption for up to 2 years, preferably for up to 1 year, and 7 to 3 hormone-containing daily units B to be taken without interruption immediately subsequently. It is, however, also possible for the dosage form according to the invention to comprise 42 to 52 or 77 to 193 hormone-containing daily units A and the final 7 to 3 hormone-containing daily units, namely the daily units B, to be taken immediately subsequently.

The hormone-containing daily units of the dosage form according to the invention in each case contain the same content of a gestagen having a contraceptive action as the only hormone component. The gestagen-containing daily units A or B to be used according to the invention preferably in each case contain a gestagen, preferably the same gestagen, in an amount which at least corresponds to the ovulation inhibition dose. The amount of gestagen is particularly preferably up to 150% above the ovulation inhibition dose.

Gestagens which are suitable for the hormone-containing daily units A or B of the dosage form according to the invention are preferably selected from the group comprising norethisterone, norethisterone acetate, norethisterone enantate, norgestimate, norgestrel, levonorgestrel, gestodene, hydroxyprogesterone caproate, medroxyprogesterone acetate, megestrol acetate, chlormadinone acetate, lynestrenol, cyproterone acetate, drospirenone, dienogest, desogestrel, progesterone, dydrogesterone, medrogestone, ethynodiol, ethynodiol diacetate, promegestone, nomegestrol acetate, trimegestone, etonogestrel, norelgestromin, norethynodrel and tibolone.

The hormones are preferably used in the amounts stated below:

| | |
|---|---|
| Norethisterone, norethisterone acetate | 0.5 to 2.0 mg |
| Norgestimate | 0.1 to 0.25 mg |
| Norgestrel | 0.3 to 2.0 mg |
| Levonorgestrel | 0.06 to 0.15 mg |
| Gestodene | 0.03 to 0.12 mg |
| Hydroxyprogesterone caproate | 10 to 800 mg |
| Medroxyprogesterone acetate | 5.0 to 40 mg |
| Megestrol acetate | 1.0 to 10 mg |
| Chlormadinone acetate | 1.5 to 10 mg |
| Lynestrenol | 0.8 to 3 mg |
| Cyproterone acetate | 1.0 to 10 mg |

-continued

| | |
|---|---|
| Drospirenone | 1.0 to 10 mg |
| Dienogest | 1.0 to 10 mg |
| Desogestrel | 0.06 to 0.20 mg |
| Progesterone | 400 to 2000 mg |
| Dydrogesterone | 5 to 50 mg |
| Medrogestone | 2 to 30 mg |
| Ethynodiol, ethynodiol diacetate | 0.4 to 3 mg |
| Promegestone | 0.5 to 10 mg |
| Nomegestrol acetate | 0.5 to 10 mg |
| Trimegestone | 0.1 to 10 mg |
| Etonogestrel | 0.1 to 2 mg |
| Norelgestromin | 0.1 to 2 mg |
| Norethynodrel | 0.3 to 3 mg |
| Tibolone | 1 to 10 mg |

Preferably, both the gestagen-containing daily units A and B contain 1.5 to 5 mg of chlormadinone acetate, wherein at least 21 daily units A, preferably 21 to 25 daily units A, and 3 to 7 gestagen-containing daily units B are present in the dosage form according to the invention. The dosage form according to the invention may, however, also comprise gestagen-containing daily units A for two or more years, preferably 42 to 365 gestagen-containing daily units A, wherein an uninterrupted period of taking said units is immediately followed by taking 7 to 3 gestagen-containing daily units B without interruption in each case comprising the increased amount of folic acid stated according to the invention.

The dosage form according to the invention comprises the gestagen-containing daily units A and B, preferably in the form of tablets, which are packaged in a blister pack and which preferably also comprise a taking indicator. This is in particular advantageous if the dosage form according to the invention is provided as a contraceptive corresponding to a woman's menstrual cycle.

The dosage form according to the invention may also be a constituent of a kit, wherein the kit according to the invention may comprise a plurality of the dosage forms according to the invention, especially if one dosage form comprises only one monthly female menstrual cycle. The kit may accordingly also comprise at least 13 dosage forms according to the invention corresponding to a female menstrual cycle of 28 days, such that, on each occasion after completing such a pill-taking cycle of 28 days, further taking may be ceased if a child is desired and an increased folic acid concentration is already ensured for a possible pregnancy. The kit may optionally include a calendar or a diary.

EXAMPLES

Example 1

| Composition | A) Per tablet | B) Per tablet |
|---|---|---|
| Chlormadinone acetate | 2.000 mg | 2.000 mg |
| Sodium folate | 0.050 mg | 3.000 mg |
| Povidone K30 | 3.000 mg | 3.000 mg |
| Lactose | 31.930 mg | 31.000 mg |
| Maize starch | 12.000 mg | 12.000 mg |
| Magnesium stearate | 0.500 mg | 0.500 mg |
| Highly disperse silicon dioxide | 0.500 mg | 0.500 mg |

A) Povidone K 30 (polyvinylpyrrolidone) and the folic acid sodium salt were dissolved in 600 ml of ethanol. Chlormadinone acetate (particle size 90%<50 μm), lactose and maize starch were mixed in a mixer/pelletiser (Diosna P25) for 5 min and then moistened thoroughly and mixed with said ethanolic solution. The moist composition was forced through a 3 mm screen and dried in a vacuum drying cabinet. The dried granular product was disagglomerated through a 0.6 mm screen, mixed with magnesium stearate and highly disperse silicon dioxide and pressed on a tablet press with 5 mm punches into tablets with a weight of 50 mg as daily units A.

B) As indicated under A), folio acid-containing tablets with a weight of 50 mg were produced as daily units B, wherein the folic acid sodium salt was dissolved in 600 ml of aqueous ethanol.

Tablets A and B were in each case coated with a lacquer based on methylhydroxypropylcellulose (for example Opadry YS-1-2184 manufactured by Colorcon); coating mass 2 mg per tablet.

The contraceptive dosage form according to the invention was produced by packaging 21 hormone-containing tablets A and 7 hormone-containing tablets B as 28 daily units to form a blister pack.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

What is claimed is:

1. A dosage form for hormonal contraception consisting of at least 21 hormone-containing daily units A and of 7-3 hormone-containing daily units B, the hormone component of each daily unit A and B, respectively, consists solely of a gestagen, wherein the gestagen is chlormadinone acetagte, for uninterrupted daily, oral administration of the hormone-containing daily units A, immediately followed by uninterrupted daily, oral administration of the hormone-containing daily units B to women, wherein each of the hormone-containing daily units A contains folic acid in a daily amount of 5 µg up to the minimum effective daily amount for women and each of the hormone-containing daily units B contains folic acid in a daily amount of more than 200 µg up to the maximum permissible amount of folic acid for women, and wherein both the hormone-containing daily units A and B each have a chlormadinone acetate content which at least corresponds to the ovulation inhibition dose of chlormadinone acetate.

2. A dosage form according to claim 1, wherein each of the hormone-containing daily units B contains more than 200 µg and up to 5 mg of folic acid.

3. A dosage form according to claim 1, wherein each of the hormone-containing daily units A contains the same amount of folic acid, and each of the hormone-containing daily units B likewise contains the same amount of folic acid.

4. A dosage form according to claim 1, wherein the maximum number of hormone-containing daily units A is sufficient for uninterrupted administration for at least one year and the number of hormone-containing daily units B corresponds to administration for 3 to 7 days.

5. A dosage form according to claim 4, wherein the number of hormone-containing daily units A is sufficient for uninterrupted daily administration for two years.

6. A dosage form according to claim 4, wherein the number of hormone-containing daily units A is sufficient for uninterrupted daily administration for one year.

7. A dosage form according to claim 1, wherein said dosage form comprises 21 to 25 hormone-containing daily units A and 7 to 3 hormone-containing daily units B.

8. A dosage form according to claim 1, wherein said dosage form comprises 42 to 52 hormone-containing daily units A and 7 to 3 hormone-containing daily units B.

9. A dosage form according to claim 1, wherein said dosage form comprises 77 to 193 hormone-containing daily units A and 7 to 3 hormone-containing daily units B.

10. A dosage form according to claim 1, wherein the chlormadinone acetate content is up to 150% above the ovulation inhibition dose of the chlormadinone acetate.

11. A dosage form according to claim 1, wherein both the hormone-containing daily units A and the hormone-containing daily units B each comprise the same amount of chlormadinone acetate.

12. A dosage from according to claim 1, wherein each hormone-containing daily unit A and B contains chlormadinone acetate in the amount of: 1.5 to 10 mg.

13. A dosage form according to claim 1, wherein each of the daily units A and B are in the form of a tablet.

14. A kit containing at least one dosage form for hormonal contraception according to claim 1.

15. A kit according to claim 14, wherein the kit contains a plurality of said dosage forms.

* * * * *